United States Patent [19]

Fujisaki et al.

[11] 4,444,200
[45] Apr. 24, 1984

[54] HEART PULSE RATE MEASURING SYSTEM

[75] Inventors: Iwao Fujisaki, Ichikawa; Shuichi Kosuge, Tama; Syuu Ogawa, Kasukabe; Kimihiko Sato, Funabashi; Toshimi Soeda, Tokyo, all of Japan

[73] Assignee: Senoh Kabushiki Kaisha, Tokyo, Japan

[21] Appl. No.: 299,578

[22] Filed: Sep. 4, 1981

[51] Int. Cl.³ .............................................. A61B 5/04
[52] U.S. Cl. .................................................... 128/706
[58] Field of Search ............... 128/639, 690, 702, 706, 128/707, 708, 710

[56] References Cited

U.S. PATENT DOCUMENTS

| | | | |
|---|---|---|---|
| 3,802,698 | 4/1974 | Burian et al. | 128/707 |
| 3,868,947 | 3/1975 | Holsinger | 128/639 |
| 4,007,731 | 2/1977 | Griffiths et al. | 128/710 |
| 4,083,366 | 4/1978 | Gombrich et al. | 128/706 |
| 4,221,223 | 9/1980 | Linden | 128/706 |
| 4,224,948 | 9/1980 | Cramer et al. | 128/690 |
| 4,237,903 | 9/1980 | Hofmann | 128/708 |
| 4,319,581 | 3/1982 | Cutter | 128/707 |

*Primary Examiner*—William E. Kamm
*Attorney, Agent, or Firm*—Lowe, King, Price & Becker

[57] ABSTRACT

A heart pulse rate measuring system comprises a casing, a pair of rod-shaped grip sensors extending outwardly from the opposite sides of the casing for sensing a heart pulse signal, and an electric circuit for calculating a heart pulse rate from the sensed heart pulse signal. Each of the grip sensors is composed of two conductive cylindrical electrodes arranged in an axially aligned relationship and electrically insulated from each other for obtaining a pulse rate utilizing the potentials at four points in a user's body. The electric circuit includes a differential amplifier, having a ground connection to one of the two electrodes of each sensor and two inputs for the remaining electrodes. A filter is used to eliminate noise from the output of the differential amplifier, and a computer calculates the heart rate from the output of the filter. Additionally, an AC-DC converter is connected between the differential amplifier and the computer for providing a DC signal to the computer when an output is provided by the differential amplifier. The computer responds to a predetermined DC level by starting a display indication of heart pulse rate. A timer is provided for use of the system with an exercise device and an alarm is activated at the expiration of the preset exercise time or if pulse rate deviates beyond upper or lower limits preset therefor. A printer provides a printout of time and/or pulse rate at predetermined time intervals.

5 Claims, 3 Drawing Figures

HEART PULSE RATE MEASURING SYSTEM

BACKGROUND OF THE INVENTION

This invention relates to a system for measuring heart pulse rate and, more particularly, to such a heart pulse rate measuring system having a pair of grip sensors adapted to be gripped with both hands for sensing heart pulse signals.

During an exercise, skeletal muscles are used and heart beats become faster so that more blood is pumped to replace nutrients in the skeletal muscles. For finding out how much exercise a person's body can take or his fitness level, it is important to get an accurate reading of his heart function. Heart beats produce a heart pulse signal which is relatively independent of person's movements, external temperature and other environment conditions. In order to get information on such heart function, it is common practice to measure heart pulse rate based upon such a heart pulse signal by using heart pulse signal sensors attached directly on several points of a person's body near his heart and connected through long wires to a separate measuring unit. However, this has been found to be insufficient in heart pulse rate measuring accuracy penalty and inconvenience attendant upon attachment and detachment of the sensors from the person's body.

The present invention provides a simple heart pulse rate measuring system which can make an accurate indication of heart pulse rate in a very short time simply by gripping grip sensors with both hands.

SUMMARY OF THE INVENTION

There is provided, in accordance with the present invention, a heart pulse rate measuring system which comprises a casing, a pair of rod-shaped grip sensors extending outwardly from the opposite sides of the casing for sensing a heart pulse signal, an electric circuit contained in the casing for calculating a heart pulse rate from the sensed heart pulse signal, and a display unit associated with the electric circuit for displaying the calculated heart pulse rate. Each of the grip sensors is composed of two conductive cylindrical electrodes arranged in axially aligned relationship and electrically insulated from each other. The electric circuit includes a differential amplifier having inputs from the grip sensors for amplifying the difference between the heart pulse signals applied thereto from the grip sensors, a filter circuit having an input from the differential amplifier for eliminating noises from the heart pulse signal applied thereto from the differential amplifier, a pulse generator having an input from the filter circuit for generating a rectangular pulse signal corresponding to the heart pulse signal applied thereto from the filter circuit, and a digital computer for counting pulses of the pulse signal fed thereto from the pulse generator and calculating a heart pulse rate.

Preferably, the electric circuit includes an alarm unit, and means for presetting upper and lower limit values for the calculated heart pulse rate into the digital computer. The digital computer is adapted to cause the alarm unit to provide a warning alarm when the calculated heart pulse rate exceeds the preset upper limit value or falls below the preset lower limit value.

BRIEF DESCRIPTION OF THE DRAWINGS

The present invention will be described in greater detail by reference to the following description taken in connection with the accompanying drawings, in which.

DESCRIPTION OF THE PREFERRED EMBODIMENT

Figure 1:
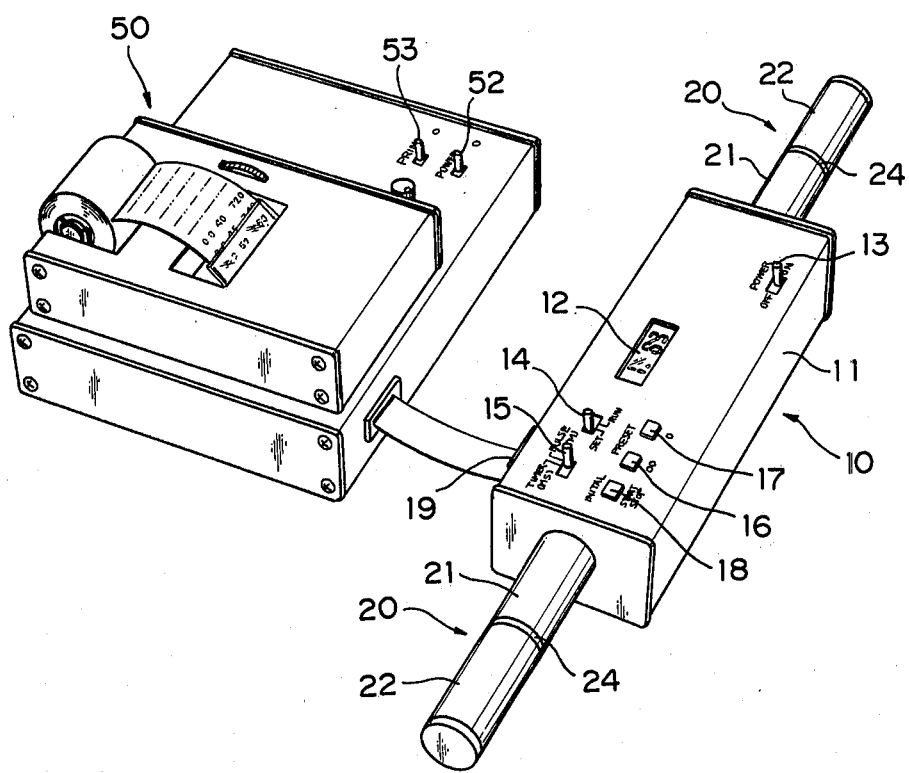
FIG. 1 is a perspective view showing one embodiment of a heart pulse rate measuring system made in accordance with the present invention, the system comprising a center unit and a digital printer.

Referring now to FIG. 1, there is illustrated one embodiment of a heart pulse rate measuring system made in accordance with the present invention. The system comprises a center unit 10 and a digital printer 50 associated with the center unit 10.

The center unit 10 comprises a casing 11 formed in its upper surface with a window 12 through which a liquid crystal display is exposed to view. The casing 11 supports on its upper surface a power switch 13, first and second mode selection switches 14 and 15, upper and lower digit preset buttons 16 and 17, and an initial button 18. The first mode selection switch 14 is movable between its RUN and SET positions, and the second mode selection switch 15 is movable between its PULSE and TIMER positions. The upper digit preset button 16 is used to select two upper digits and the lower digit preset button 17 is used to select one lower digit. The initial button 18 is used to register the selected numbers in a memory of a digital computer to be described later and also to start a timer included in the digital computer. The casing 11 supports on its side surface a connector 19 for connection to the digital printer 50. A pair of rod-shaped grip sensors 20 extends outwardly from insulating panels 28 secured on the opposite end surfaces of the casing 11.

Figure 2:
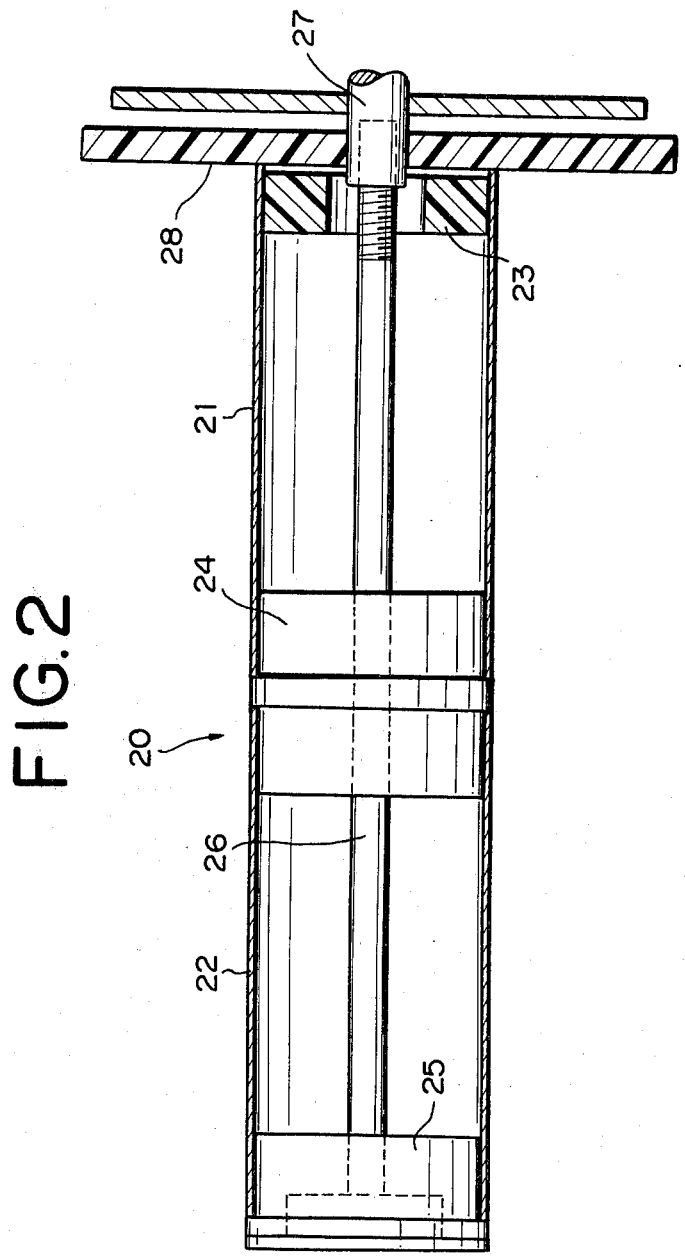
FIG. 2 is a sectional view showing one grip sensor used in the heart pulse rate measuring system of FIG. 1.

As shown in FIG. 2, each of the left- and right-hand grip sensors 20 has inner and outer cylindrical electrodes 21 and 22 which are made of a conductive material, such as for example, stainless steel. The inner electrode 21 is bonded at its inner end on a support ring 23 and at its outer end on one shoulder of a spacer 24. The outer electrode 22 is bonded at its inner end on the other shoulder of the spacer 24 and at its outer end on the shoulder of an end cap 25. A bolt 26 extends through the end cap 25, the spacer 24, and the support ring 23 and threadedly engaged with a nut 27 secured in the insulating plate 28 so as to secure them to the end surface of the casing 11. The support ring 23, the spacer 24, and the end cap 25 are made of an insulating material, such as for example, plastic. In such a manner, the inner and outer cylindrical electrodes 21 and 22 are arranged in axially aligned relationship and electrically insulated from each other. The inner and outer electrodes 21 and 22 are connected to an electric circuit to be described later through separate electric cords extending therefrom into the casing 11.

When a person grips the left- and right-hand grip sensors 20 with both hands, preferably with the center of his palms covering the spacers 24 between the inner and outer electrodes 21 and 22, the inner and outer electrodes 21 and 22 catch heart pulse signals caused by heart beats together with AC hum and human body hum (hereinafter referred merely to as noises).

Figure 3:
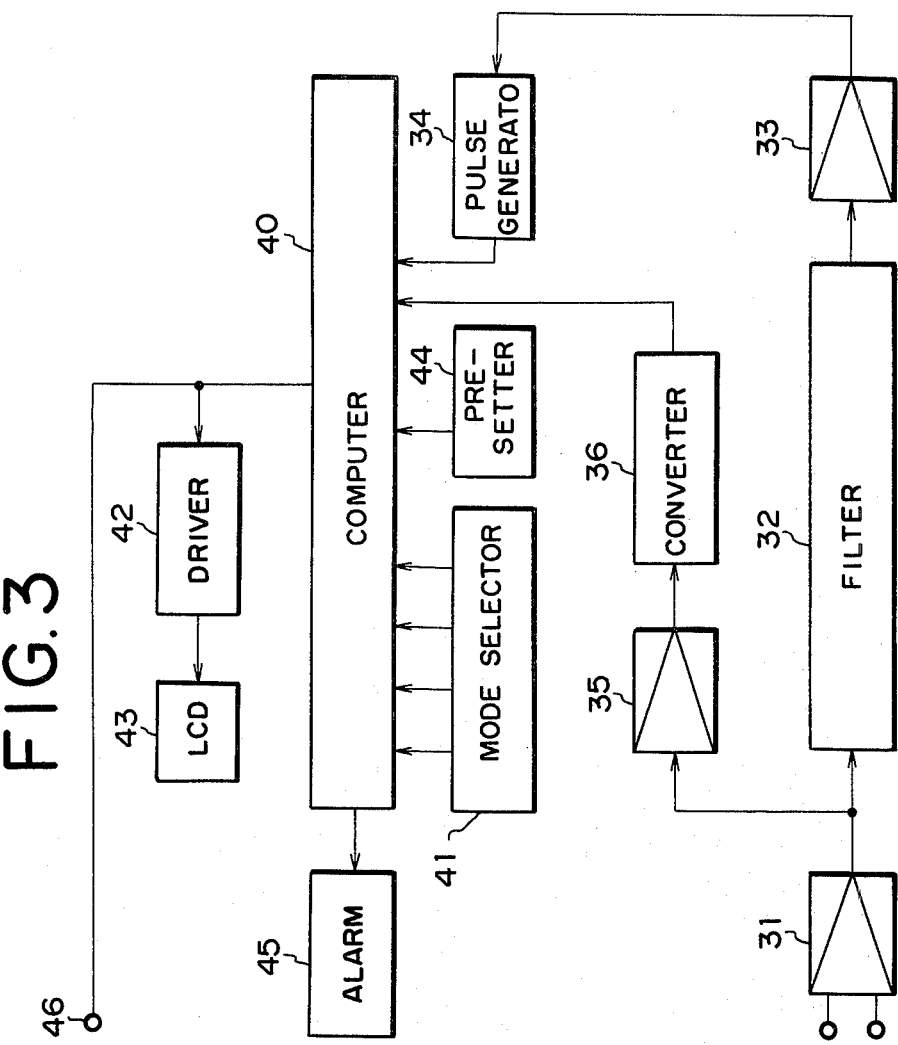
FIG. 3 is a block diagram showing an electric circuit used in the center unit.

Referring to FIG. 3, there is illustrated an electric circuit, which is generally designated at 30, contained in the casing 11 of the center unit 10. The electric circuit 30 includes a differential amplifier 31 which has its one input coupled to the outer cylindrical electrode 22 of the left-hand grip sensor 20, the other input thereof being connected to the outer cylindrical electrode 22 at the right-hand grip sensor 20. The inner cylindrical electrodes 21 of the left- and right-hand grip sensors 20 are coupled to the ground terminal of the differential amplifier 31. The differential amplifier 31 amplifies the difference between the voltages applied to the inputs thereof. This is effective to reduce the noises introduced into the heart pulse signals fed to the differential amplifier 31 from the grip sensors 20. The output of the differential amplifier 31 is then coupled to a filter circuit 32 which further reduces or eliminates the noises still included in the heart pulse signal from the differential amplifier 31. The output of the filter circuit 32 is fed through an amplifier 33 to a pulse generator 34 which generates a rectangular pulse signal related to the pulse signal from the amplifier 33. That is, the pulse generator 34 provides a train of pulses corresponding to the heart beats of the person.

The electric circuit 30 also comprises a digital computer 40 operable in several modes one of which is selectively set by a mode selector 41 comprised of the first and second mode selection switches 14 and 15. If the first mode selector switch 14 is in its RUN position and the second mode selection switch 15 is in its PULSE position, the digital computer 40 is placed in a pulse rate measuring mode to count the pulses from the pulse generator 34 and calculate the heart pulse rate, which corresponds to the rate of heart beats occurring in a minute, within five or six seconds. The digital computer 40 provides a command signal to a driver 42 which thereby makes an indication of the calculated heart pulse rate on a liquid crystal display 43. When the first mode selector switch 14 is in its RUN position and the second mode selection switch 15 is in its TIMER position, the digital computer 40 operates as a timer and indicates, on the liquid crystal display 43, the elapsed time at every second after the initial button 18 is depressed once. When the initial button 18 is depressed twice, the time display stops and keeps on displaying the value. When the initial button 18 is depressed for the third time, the time indication returns to zero.

The digital computer 40 may be associated with a presetter 44, which is comprised of the upper and lower digit present buttons 16 and 17 and the initial button 18, for presetting upper and lower limit values for calculated heart pulse rate. The upper limit value may be preset at the maximum heart pulse rate above which it will become dangerous to continue to exercise. The lower limit value may be selected at the minimum heart pulse rate below which the exercise will not achieve the desired effects. The digital computer 40 is placed in its first preset mode of operation if the first mode selection switch 14 is placed in its SET position and the second mode selection switch 15 is placed on its PULSE position. Under this condition, the upper and lower values can be preset separately by continuously depressing the upper and lower digit preset buttons 16 and 17 until desired numbers for the upper and lower limit values appear on the liquid crystal display 43 and then depressing the initial button 18 to register the numbers in the memory of the digital computer 40.

The digital computer 40 is placed in its second preset mode of operation when the first mode selection switch 14 is in its SET position and the second mode selection switch 15 is in its TIMER position. Under this condition, a desired exercise time can be preset by continuously depressing the upper and lower digit preset buttons 16 and 17 until desired numbers for the desired exercise time appear on the liquid crystal display 43 and thereafter depressing the initial button 18 to register the number in the memory of the digital computer 40.

When the calculated pulse rate exceeds the preset upper limit value, the calculated pulse rate falls below the preset lower limit value, or the elapsed exercise time exceeds the preset value, the digital computer 40 provide a warning signal to an alarm 45 which thereby provides a warning alarm such as sounding a buzzer.

The output of the differential amplifier 31 is also coupled through a tough-sensor amplifier 35 to an AC-DC converter 36 and hence to the digital computer 40. The AC-DC converter 36 converts the AC signal from the differential amplifier 31 into a corresponding DC signal. In response to the DC signal from the AC-DC converter 36, the digital computer 40 makes a determination as to whether or not any person grips the grip sensors 20 with his both hands. This may be used to start operation of the digital computer 40 to make a heart pulse rate indication when it detects any person gripping the grip sensors 20.

The command signal from the digital computer 40 to the driver 42 is also coupled to an output terminal 46 for connection to the digital printer 50. The digital printer 50 contains therein a timer (not shown) for printing out, on a tape 51, the values displayed on the liquid crystal display 43 together with the elapsed exercise time provided by the timer at a predetermined time interval. The reference numeral 52 designates a power switch, and the numeral 53 designates a print start switch.

The operation of the heart pulse rate measuring system of the present invention will now be described. Assuming first that a person desires to know his heart pulse rate during or immediately after an exercise, he turns the first mode selection switch 14 to its RUN position and the second mode selection switch 15 to its PULSE position. When he grips the grip sensors 20 with his both hands, heart pulse signals are applied to the inputs of the differential amplifier 31. The output of the differential amplifier 31 is applied through the filter circuit 32 and the amplifier 33 to the pulse generator 34. The heart pulse signal applied from the amplifier 33 to the pulse generator is free from noises. The pulse generator 34 converts the heart pulse signal into a corresponding rectangular pulse signal which is fed to the digital computer 40. The digital computer 40 counts the pulses from the pulse generator 34 and calculates a heart pulse rate within five or six seconds. The calculated heart pulse rate is displayed on the liquid crystal display 43 through the driver 42. The calculated heart pulse rate is also printed out by the digital printer 50 with the elapsed exercise time at a predetermined time interval.

If upper and lower limit values for heart pulse rate and a desired value for elapsed exercise time are previously preset by the use of the presetter 44, the alarm 45 will provide a warning alarm when the calculated pulse rate exceeds the preset upper limit value, the calculated pulse rate falls below the preset lower limit value, or the elapsed exercise time exceeds the preset value.

There has been provided, in accordance with the present invention, a simple heart pulse rate measuring system capable of making an accurate indication of heart pulse rate in a very short time simply by gripping grip sensors with both hands. While the present invention has been described in conjunction with a specific embodiment thereof, it is evident that many alternatives, modifications and variations will be apparent to those skilled in the art. Accordingly, it is intended to embrace all alternatives, modifications and variations that fall within the spirit and broad scope of the appended claims.

What is claimed is:

1. An apparatus for measuring the heart pulse rate of a user, comprising:
   (a) a casing;
   (b) a pair of rod-shaped grip sensors extending outwardly from the opposite sides of said casing, each of said grip sensors being composed of first and second cylindrical conductive electrode means arranged in axially aligned relationship and electrically insulated from each other for sensing a heart pulse signal utilizing potentials at four points on the user's body, obtained when the user grips both of said first and second electrode means of each said grip sensor with one hand; and
   (c) an electric circuit contained in said casing, said electric circuit including:
      a differential amplifier having a common ground electrically connected to said first conductive electrode means of each of said grip sensors and a pair of additional inputs respectively electrically connected to said second electrode means of each of said grip sensors for providing an output corresponding to a difference between the heart pulse signals from said grip sensors;
      a filter circuit means having an input from said differential amplifier for eliminating noises from the heart pulse difference signal applied thereto from said differential amplifier;
      a digital computer means responsive to an input from said filter circuit means for calculating a heart pulse rate;
      a display means associated with said digital computer means for displaying the calculated heart pulse rate;
      an AC-DC converter connected between said differential amplifier and said digital computer means for converting an AC signal from said differential amplifier into a corresponding DC signal; and
      said digital computer means including means sensitive to the DC signal from said AC-DC converter for causing said display means to start displaying the calculated heart pulse rate thereon.

2. The apparatus of claim 1, wherein said electrical circuit includes an alarm unit connected to said digital computer means and means for presetting upper and lower limit values for the calculated heart pulse rate into said digital computer means, and wherein said digital computer means includes means for causing said alarm unit to provide a warning alarm when the calculated heart pulse rate exceeds the preset upper limit value or falls below the preset lower limit value.

3. The apparatus of claim 2, wherein said electric circuit includes means for presetting a desired exercise time into said digital computer means, and wherein said digital computer means includes means for causing said alarm unit to provide a warning alarm when the elapsed exercise time exceeds the preset exercise time.

4. The apparatus of claim 1, which further comprises a digital printer means associated with said digital computer means for printing out the calculated heart pulse rate at predetermined time intervals.

5. The apparatus of claim 4, wherein said digital printer means contains a timer for printing out the calculated heart pulse rate together with elapsed exercise time.

* * * * *